United States Patent
Chen et al.

(10) Patent No.: US 11,291,454 B2
(45) Date of Patent: Apr. 5, 2022

(54) LEFT ATRIAL APPENDAGE CLOSURE APPARATUS

(71) Applicant: SHENZHEN KYD BIOMEDICAL TEHCNOLOGY CO. LTD., Shenzhen (CN)

(72) Inventors: YiLong Chen, Shenzhen (CN); Wei Huang, Shenzhen (CN)

(73) Assignee: SHENZHEN KYD BIOMEDICAL TECHNOLOGY CO. LTD., Shenzhen (CN)

(*) Notice: Subject to any disclaimer, the term of this patent is extended or adjusted under 35 U.S.C. 154(b) by 79 days.

(21) Appl. No.: 16/067,445

(22) PCT Filed: Dec. 26, 2016

(86) PCT No.: PCT/CN2016/112062
§ 371 (c)(1),
(2) Date: Jun. 29, 2018

(87) PCT Pub. No.: WO2017/114348
PCT Pub. Date: Jul. 6, 2017

(65) Prior Publication Data
US 2019/0021741 A1    Jan. 24, 2019

(30) Foreign Application Priority Data
Dec. 29, 2015 (CN) .......................... 201511003714.9

(51) Int. Cl.
*A61B 17/12* (2006.01)
*A61L 31/06* (2006.01)
(Continued)

(52) U.S. Cl.
CPC .... *A61B 17/12122* (2013.01); *A61B 17/0057* (2013.01); *A61B 17/12031* (2013.01);
(Continued)

(58) Field of Classification Search
CPC .......... A61B 17/0057; A61B 17/12031; A61B 17/12122; A61B 17/12145;
(Continued)

(56) References Cited

U.S. PATENT DOCUMENTS 5,000,743 A    3/1991  Patel
5,932,299 A *  8/1999  Katoot ................... A61L 27/34
                                                    427/385.5
(Continued)

FOREIGN PATENT DOCUMENTS

CN    1342056 A    3/2002
CN    1711978 A    12/2005
(Continued)

OTHER PUBLICATIONS

International Search Report and Written Opinion. in corresponding PCT Application No. PCT/CN2016/112062, dated Mar. 27, 2017.
(Continued)

*Primary Examiner* — Alexander J Orkin
(74) *Attorney, Agent, or Firm* — Leason Ellis LLP

(57) ABSTRACT

A left atrial appendage closure apparatus for obstructing the left atrial appendage, comprises a sealing plate and an anchor plate. The sealing plate is a mesh structure and arranged with a choke membrane inside. In addition, the sealing plate adopts a tubular member for distal fixation and is connected with the anchor plate by the tubular member. The proximal end of the sealing plate is fixed with a fastener and is provided with a structure to connect to a convey device. The end of the tubular member at the other side away from the end connected to the sealing plate is arranged with a plurality of supporting rods, which intersect radially to form the anchor plate.

20 Claims, 8 Drawing Sheets

(51) Int. Cl.
*A61B 17/00* (2006.01)
*A61L 31/14* (2006.01)
(52) U.S. Cl.
CPC .. *A61B 17/12172* (2013.01); *A61B 17/12177* (2013.01); *A61L 31/06* (2013.01); *A61L 31/14* (2013.01); *A61B 17/12145* (2013.01); *A61B 2017/00575* (2013.01); *A61B 2017/00579* (2013.01); *A61B 2017/00592* (2013.01); *A61B 2017/00597* (2013.01); *A61B 2017/00615* (2013.01); *A61B 2017/00938* (2013.01); *A61L 2400/18* (2013.01)

(58) Field of Classification Search
CPC ........ A61B 17/12172; A61B 17/12177; A61B 2017/00575; A61B 2017/00597; A61B 2017/00615; A61B 2400/18
See application file for complete search history.

(56) References Cited

U.S. PATENT DOCUMENTS

| | | | | |
|---|---|---|---|---|
| 6,306,419 | B1* | 10/2001 | Vachon | A61K 9/7023 424/422 |
| 6,652,556 | B1* | 11/2003 | VanTassel | A61B 17/12136 606/200 |
| 2002/0111647 | A1* | 8/2002 | Khairkhahan | A61B 17/0057 606/200 |
| 2004/0225324 | A1* | 11/2004 | Marino | A61B 17/0057 606/213 |
| 2005/0192627 | A1* | 9/2005 | Whisenant | A61B 17/0057 606/213 |
| 2007/0073337 | A1* | 3/2007 | Abbott | A61B 17/0057 606/213 |
| 2007/0232992 | A1* | 10/2007 | Kutsko | A61B 17/12022 604/30 |
| 2008/0213611 | A1* | 9/2008 | Asgari | A61L 27/04 428/566 |
| 2008/0215085 | A1* | 9/2008 | Whisenant | A61B 18/1492 606/213 |
| 2009/0062838 | A1* | 3/2009 | Brumleve | A61B 17/12022 606/198 |
| 2010/0198254 | A1* | 8/2010 | Schaeffer | A61B 17/0057 606/213 |
| 2012/0083832 | A1* | 4/2012 | Delaloye | A61B 17/0057 606/213 |
| 2012/0172927 | A1* | 7/2012 | Campbell | A61B 17/0057 606/213 |
| 2013/0046339 | A1* | 2/2013 | Greenberg | A61B 17/0057 606/213 |
| 2013/0253663 | A1* | 9/2013 | Amoroso | A61L 27/18 623/23.75 |
| 2014/0046347 | A1* | 2/2014 | Cully | A61B 17/064 606/151 |
| 2014/0141048 | A1 | 5/2014 | Rolf et al. | |
| 2015/0005810 | A1* | 1/2015 | Center | A61B 17/12177 606/200 |
| 2015/0173883 | A1* | 6/2015 | Ingber | A61L 29/16 435/287.2 |

FOREIGN PATENT DOCUMENTS

| | | |
|---|---|---|
| CN | 1799521 A | 7/2006 |
| CN | 101146570 A | 3/2008 |
| CN | 102805654 A | 12/2012 |
| CN | 103099652 A | 5/2013 |
| CN | 103347448 A | 10/2013 |
| CN | 203634235 U | 6/2014 |
| CN | 104287804 A | 1/2015 |
| CN | 104352261 A | 2/2015 |
| CN | 104398284 A | 3/2015 |
| CN | 204181679 U | 3/2015 |
| CN | 204246182 U | 4/2015 |
| CN | 104856741 A | 8/2015 |
| CN | 105147350 A | 12/2015 |
| EP | 1842490 A1 | 10/2007 |
| EP | 2716237 A1 | 4/2014 |
| EP | 2952157 A1 | 12/2015 |
| JP | 2017500908 A | 1/2017 |
| JP | 6529137 B2 | 6/2019 |
| RU | 2405473 C2 | 12/2010 |
| RU | 128101 U1 | 5/2013 |
| RU | 2514532 C2 | 4/2014 |
| RU | 2013126872 A | 12/2014 |

OTHER PUBLICATIONS

Extended European Search Report in corresponding European Application No. 16881137.0, dated Nov. 12, 2019.
Russian Office Action in corresponding Russian Application No. 2018123605/14, dated Mar. 10, 2020 (with English translation).
Russian Search Report in corresponding Russian Application No. 2018123605/14, dated Mar. 10, 2020.
Examination Report in corresponding Australian No. 2016381148, dated Feb. 8, 2021.
Russian Office Action in corresponding Russian Application No. 2018123605/14, dated Jul. 21, 2020 (with English translation).
Brazilian Office Action in corresponding Brazilian Application No. BR112018013077-0, dated Jun. 18, 2020 (with English translation).
Examination Report in corresponding Indonesian Application No. P00201805574, dated Jul. 16, 2020 (with English translation).
Second Examination Report in corresponding Indonesian Application No. P00201805574, dated May 24, 2021.

* cited by examiner 1 day         1 month

LEFT ATRIAL APPENDAGE CLOSURE APPARATUS

CROSS-REFERENCE TO RELATED PATENT APPLICATIONS

This application is a U.S. National Phase Application under 35 U.S.C. § 371 of International Patent Application No. PCT/CN2016/112062, filed Dec. 26, 2016, and claims the priority of Chinese Application Nos. 201610119169.8, Mar. 2, 2016 and 201511003714.9, filed Dec. 29, 2015, all of which are incorporated by reference in their entireties. The International Application was published on Jul. 6, 2017 as International Publication No. WO 2017/114348 A1.

TECHNICAL FIELD

The present invention relates to an implantable medical device and in particular relates to a highly effective left atrial appendage closure apparatus. The apparatus can be deployed repeatedly and stably fixed. It is fatigue-resistant and can occlude the left atrial appendage and obstruct the outflow of thrombus in the left atrial appendage.

BACKGROUND ART

At present, with the development of the interventional apparatus, many untreatable diseases with surgery have been treated. Compared with surgical treatment, the interventional therapy possesses the advantages of less trauma, faster recovery and better efficacy. During the past half century, the interventional therapy has been developed rapidly, and various kinds of interventional medical devices have also been created to be used for treating more and more diseases and patients.

Atrial fibrillation (AF) is one of the most common arrhythmias. Apart from the discomfort brought by the symptom of palpitation, the occurrence of the thromboembolism and other complications are the main hazards of atrial fibrillation. Among the patients with non-valvular and non-rheumatic atrial fibrillation, about 90% of the thrombus originate from the left atrial appendage. Every year, the thromboembolic events and stroke occur in approximately 5% patients with atrial fibrillation. The fatality rate caused by stroke is up to 50%. Therefore, it is of important clinical significance to know how to prevent and treat the stroke caused by atrial fibrillation thromboembolism. At present, the prevention and treatment methods of atrial fibrillation thrombus include surgeries, drug treatment and interventional therapy. Among all the methods, the occlusion of left atrial appendage by surgical procedure has not been widely used because of its great trauma and high risk. At present, the most common means to prevent stroke in patients with atrial fibrillation is receiving long-term oral anticoagulant drugs, but the anticoagulant drugs will induce the bleeding risk and about 14% to 44% of patients fail to receive long-term anticoagulant therapy because of contraindications. In recent years, a most advanced interventional therapy has been developed at home and abroad. Through a tiny catheter, the tailor-made left atrial appendage closure apparatus is implanted into the left atrial appendage to occlude the left atrial appendage and to prevent and treat thrombus events and stroke in patients with atrial fibrillation. This therapy has become the first choice for the prevention and treatment of stroke caused by atrial fibrillation with the advantages of small trauma, low risk, quick recovery and good efficacy.

Currently, this kind of instrument can be categorized into braiding, cutting and hybrid types from the view of structure. These types of left atrial appendage closure apparatus can all be inserted into the left atrial appendage through catheter intervention to achieve the occlusion effect of the left atrial appendage, but considerable limitations exist among all of them. The left atrial appendages are complex in anatomical structures and different in shape from person to person, including the elliptical and peanut shapes, etc. The inner wall of the left atrial appendage is uneven, the shape is irregular and the wall is thin, so it is difficult to realize both the non piercement of the wall and the solid fixation inside the left atrial appendage without falling off, and ultimately achieve the ideal occlusion effect.

For example, the braided-type left atrial appendage closure apparatus relates to the invention of patents CN1799521A and CN101146570A. They anchored the closure apparatus by using the uneven structure on the surface of the fixation plate of the closure apparatus and applying the sealing plate at the opening of the left atrial appendage to achieve the effect of occlusion. The advantages of this design are simple in structure, less difficulty in processing and low in cost. But the lower anchorage strength of the braided fixation plate makes it difficult to adapt to the different shapes of the left atrial appendage. Even if the anchor hook is sutured on the fixation plate, the fixation plate is also difficult to penetrate into the left atrial appendage wall under the condition of the extrusion deformation to achieve the stable fixation. Moreover, the shape of the sealing plate will be affected by the extrusion deformation of fixed plate in the left atrial appendage, which leads to the poor sealing effect.

For example, the cutting-type left atrial appendage closure apparatus relates to the invention of patents CN1711978A and CN1342056A. The nickel titanium metal tubes are cut and formed into the designed shape by thermal treatment and processing. An outward anchor pin is designed in the part in contact with the inner wall of the left atrial appendage to penetrate into the inner wall of the left atrial appendage to achieve stable fixation. Generally speaking, a choke membrane is usually sutured on the cut-type mesh frame to achieve the effect of left atrial appendage occlusion. The advantage of this structure design is that the whole closure apparatus is integrated and rigid, which makes it easy to be fixed inside the left atrial appendage. The anchor pins designed are easy to pierce into the inner wall of the left atrial appendage for stable fixation and prevention of closure apparatus from falling off. However, the cutting type of left atrial appendage closure apparatus is limited in the deformation capacity and fails to adapt to left atrial appendages with various shapes, which limit its application to a great extent. After the cutting-type left atrial appendage closure apparatus is inserted into the left atrial appendage, the part in the left atrial appendage will usually form a depression with the atrial wall to form a new "left atrial appendage area", which will increase the risk of new thrombosis. The anchor pins of the cut-type left atrial appendage closure apparatus are usually penetrated to the left atrium to stabilize the closure apparatus and prevent the closure apparatus from falling off. But the anchor pins penetrated to the left atrium will be stuck to the edge of the sheath wall during the repeated positioning and the closure apparatus retrieval to induce the failure of closure apparatus retrieval and repeated positioning.

For example, the hybrid-type left atrial appendage closure apparatus relates to the invention of patents CN102805654A and CN103099652A. In these designs, the sealing plate adopts a braided type and the choke membrane is usually sutured in the sealing plate to occlude the left atrial appendage. The fixation plate is made by cutting nickel titanium metal tubes and forms into the designed shape by thermal treatment and processing. In the part in contact with the inner wall of the left atrial appendage, there are outward anchor pins penetrating into the inner wall of the left auricle to achieve stable fixation. The hybrid-type left atrial appendage closure apparatus effectively solves most of the problems existing in the cutting-type of left atrial appendage closure apparatus. However, the sealing plate related to CN102805654A possesses a plane structure, which is not suitable for the sealing in the arc structure of the left atrium; in addition, the supporting rods of the anchor plate connect with each other and the deformation of the joint parts is large, which will induce large processing difficulty, poor fatigue resistant performance, brittleness in the human body and further resulting in the risk of cardiac perforation. In addition, an anchor pin in the fixation plate of CN103099652A usually penetrates to the left atrium to stabilize the closure apparatus and prevent the closure apparatus from falling off. But the anchor pins penetrating into the left atrium will be stuck to the edge of the sheath wall in the process of repeated positioning and the closure apparatus retrieval, which leads to the failure of repeated positioning and the closure apparatus retrieval. Moreover, the fixation plate of the hybrid-type left atrial appendage closure apparatus usually has large deformation to reverse the direction of the anchor pin, which results in the tension and the shape variable of the fixation plate to reach the extreme of the material. This instrument has poor fatigue strength in permanent implantation, is easy to break and pierce the heart and other tissues to further threaten the life of the patients.

Moreover, CN104352261A discloses an improved structure of the left atrial appendage closure apparatus, in which the connecting plate provides support for the anchor plate to form a rigid structure to enlarge the deformation and increase the processing difficulty. In addition, the plane structure of the anchor plate is larger than the diameter of the anchor plate in the processes of expansion and retrieval, which makes it easy to pierce the heart and other tissues and threaten the life. FIG. 11 is a diagrammatic sketch of the structure in opening status.

Therefore, considering the advantages and disadvantages of all kinds of left atrial appendage closure apparatus, it is very urgent to develop a left atrial appendage closure apparatus, which can effectively occlude the left atrial appendage, be deployed repeatedly, stably fixed and permanently implanted.

BRIEF SUMMARY OF THE INVENTION

Some embodiments aim to provide an effective, repositionable, stably fixed and fatigue resistant left atrial appendage closure apparatus for occluding the left atrial appendage (LAA) and blocking the outflow of thrombus in the left atrial appendage.

For this purpose, the embodiments of the present invention provide a technical scheme for providing a left atrial appendage closure apparatus, comprising a sealing plate and an anchor plate connected to the sealing plate.

The sealing plate is a mesh structure and arranged with a choke membrane inside, the sealing plate's distal end is connected to a tubular member and is connected with the anchor plate by the other end of the tubular member which is opposite the end fixed to the sealing plate, the proximal end of the sealing plate is fixed with a fastener and has a structure that can be connected to a convey device.

The end of the tubular member at the other side away from the end fixed to the sealing plate is arranged with a plurality of supporting rods. The supporting rods originate from the direction away from the sealing plate and the proximal ends of the supporting rods cross the center of the tubular member to the opposite side without extending into the lumen of the tubular member. The supporting rods intersect radially to form the anchor plate. The angle α between the center axis of the tubular member and the proximal ends of the supporting rods is 40-55° and the distal ends of the supporting rods are in an inwardly curved shape. On the condition that the sealing plate and anchor plate are expanded, the height of the whole closure apparatus is 12-20 millimeters, the height of the anchor plate is 9-15 millimeters, and the height of the sealing plate is 3-5 millimeters.

According to the aforementioned preferred structure design, the anchor plate of the left atrial appendage closure apparatus of the embodiment is in a depression shape, which helps to deploy and retrieve the anchor plate with the sheath tube of the convey device. When the sheath tube deploys or retrieves the closure apparatus, the anchor plate in depression shape in the folding process has a diameter not larger than that in the expansion process, which enables the anchor plate to slowly fold into the sheath tube of the convey device so as to avoid the damage of left atrial appendage and improve the safety efficiency.

Preferably, the length of the distal inward bending part of the supporting rods is 1-5 millimeters. The number of the supporting rods is a natural number selected from 2 to 50, which is preferred as an odd number. The inward bending part of the distal end of at least one supporting rod has more than one anchor pin on the side near the auricle. The extendable angle between the anchor pin and the supporting rod is 20-45 degrees. On the condition that the anchor plate is expanded, the anchor plate is capable of pressing against the inner wall of the left atrial appendage, and the anchor pin is capable of penetrating into the inner wall of the left atrial appendage to stabilize the anchor plate in the left atrial appendage, which achieves a good fixation effect of the anchor plate made of the supporting rods in the interior of the left atrial appendage.

The distal end of the supporting rod is provided with a round ball head. The proximal end of the sealing plate is fixed with the fastener and the structure of the fastener for connecting with the convey device is a screw thread structure. The round ball head may prevent the end of the supporting rod from damaging the left atrial during deployment or retrieval. The arranged screw thread structure is beneficial to the transmission, expansion and retrieval of the left auricle closure apparatus.

The sealing plate is slightly larger than the anchor plate in diameter. When the sealing plate is 2-6 mm larger than the anchor plate in diameter, it is suitable for the single lobe left atrial appendage. When the sealing plate is 6-12 mm larger than the anchor plate in diameter, it is more suitable for the dual-lobe left atrial appendage. The closure apparatus can fit the structure of the left atrial appendage. Therefore, the application range is broader.

When making the left atrial appendage closure apparatus, the root of the anchor pin may be on the supporting rod. The shape of the anchor pin is laser-cut and the angle of the anchor pin is achieved by thermal treatment with a mould. The anchor pin extends automatically outwards in the absence of pressure and retracts onto the supporting rod when under pressure. The sealing plate and the anchor plate adopt the memorable alloy material, wherein the nitinol wire is preferred to form into the desired shape by thermal treatment. The tubular member is selected from steel sleeves or other types of alloy sleeves.

The further preferred embodiment is that the supporting rods have holes to be used to suture the PET (polyethylene terephthalate) choke membrane onto the anchor plate to prevent the outflow of thrombus in the left atrial appendage.

The choke membrane may be an unmodified or chemically modified PET choke membrane.

The PET choke membrane may be a chemically modified PET choke membrane, which has an amide group by an exchange reaction with an ester group. The contact angle of the chemically modified PET choke membrane is less than 90 degrees, which enhances the hydrophilicity. The chemical treatment of the surface of the choke membrane induces the surface negative ionization, which not only reduces the platelet adhesion on the surface of the sealing plate, but also improves the hydrophilicity and biological compatibility of the choke membrane as well as achieves rapid endothelialization. The endothelialization degree in a short period is much higher than that of the unmodified PET choke membrane, which reduces the closure apparatus associated thrombosis risks.

Specifically, the PET choke membrane makes use of the reaction to replace the ester group for the amide group to graft the molecule with sodium sulfonate group on the surface of the choke membrane, so that the PET choke membrane becomes electronegative. This kind of PET choke membrane can adsorb the toluidine blue dye with positive electrical charge.

The chemical modification method of the PET choke membrane is as follows: placing a PET choke membrane in a proper container, adding a mixed solvent of water and 1, 4-dioxane, adding an alkane with both a terminal amino group and terminal sulfonic group, adding a catalyst, stirring for 2-24 hours at 50-100° C. and removing the choke membrane after the reaction.

The mentioned alkane with the sulfonic group is selected from 3-amino propane sulfonic acid, 4-amino butane sulfonic acid, 5-amidopentane sulfonic acid and 6-amino hexane sulfonic acid.

The catalyst is selected from sodium hydroxide, potassium hydroxide or ammonia water.

In a more specific preferred embodiment: the volume ratio of water to 1,4-dioxaneis is 5:1. After the reaction is finished, the choke membrane is removed and washed repeatedly by deionized water and absolute alcohol.

For example, a chemical modification method of a PET choke membrane is as follows: placing 50 pieces of PET choke membranes in a 250 mL of round bottom flask, adding 200 mL of a mixed solvent of water and 1, 4-dioxane with the volume ratio of 5:1, adding 0.5 g of an alkane with both a terminal amino group and terminal sulfonic group, and 1 g of catalyst, stirring for 2-24 hours at 50-100° C., removing the choke membrane after reaction, and washing 5 times repeatedly by deionized water and anhydrous alcohol.

Compared with the existing technology, the embodiments of the present invention possess the following advantages:

The anchor plate of the left atrial appendage closure apparatus according to the invention is in a depression shape, which helps the sheath tube of the convey device to deploy and retrieve the anchor plate. When the closure apparatus is deployed or retrieved by the sheath tube, the anchor plate in the depression shape has the smaller diameter in the folding process than in the expansion process, which enables the anchor plate to slowly fold into the sheath tube of the convey device so as to avoid the damage of the left atrial appendage and improve the safety efficiency.

The anchor plate of the left atrial appendage closure apparatus according to the invention has little structure deformation, is stable, and has excellent fatigue resistance for permanent implantation and adaptable to the left atrial appendage cavity with various shapes and sizes.

The two-part design of the left atrial appendage closure apparatus according to the present invention enables the closure apparatus to adapt to various forms and dimensions of the left atrial appendage.

The left atrial appendage closure apparatus according to the invention has the advantages of stable anchorage and effective occlusion of the left atrial appendage.

The left atrial appendage closure apparatus according to the invention is applicable to not only occlude the single lobe left atrial appendage, but also occlude the dual-lobe left atrial appendage.

The left atrial appendage closure apparatus according to the invention is repositionable. In some cases, if the placement is not good enough, the closure apparatus can be retrieved to the sheath tube, and repositioned without removing from a pushing rod until the satisfactory anchoring and occlusion effects are achieved, which greatly reduces surgery risks.

The left atrial appendage closure apparatus according to the invention can use a small conveying system to further reduce the damage to the blood vessel by the convey devices in the surgery process.

The left atrial appendage closure apparatus according to the invention is flexibly connected with the pushing rod, which greatly reduces the tension exerted by the convey device such as the pushing rod to the closure apparatus and makes the placement of the closure apparatus more accurate and precise.

The choke membrane of the left atrial appendage closure apparatus according to the invention is chemically treated to generate the negative surface ionization, which not only reduces the platelet adhesion on the surface of the sealing plate, but also improves the hydrophilicity and biological compatibility of the choke membrane as well as achieves rapid endothelialization. The endothelialization degree in a short period of time is much higher than that of the unmodified PET choke membrane, which reduces the closure apparatus associated thrombosis risks.

The present invention will become clearer with the following description in combination with the accompanying drawings, which are used to explain the embodiments of the invention.

BRIEF DESCRIPTION OF THE SEVERAL VIEWS OF THE DRAWINGS

In FIG. 4.

1 positioned in the anatomical structure of the dual-lobe left atrial appendage.

In FIG. 5.

FIG. 10 is a postoperative anatomic image.

DETAILED DESCRIPTION OF SEVERAL EMBODIMENTS OF THE INVENTION

The embodiments of the invention are described with references to the accompanying drawings. The similar element symbols in the attached drawings represent the similar elements.

Embodiment 1

Figure 1:
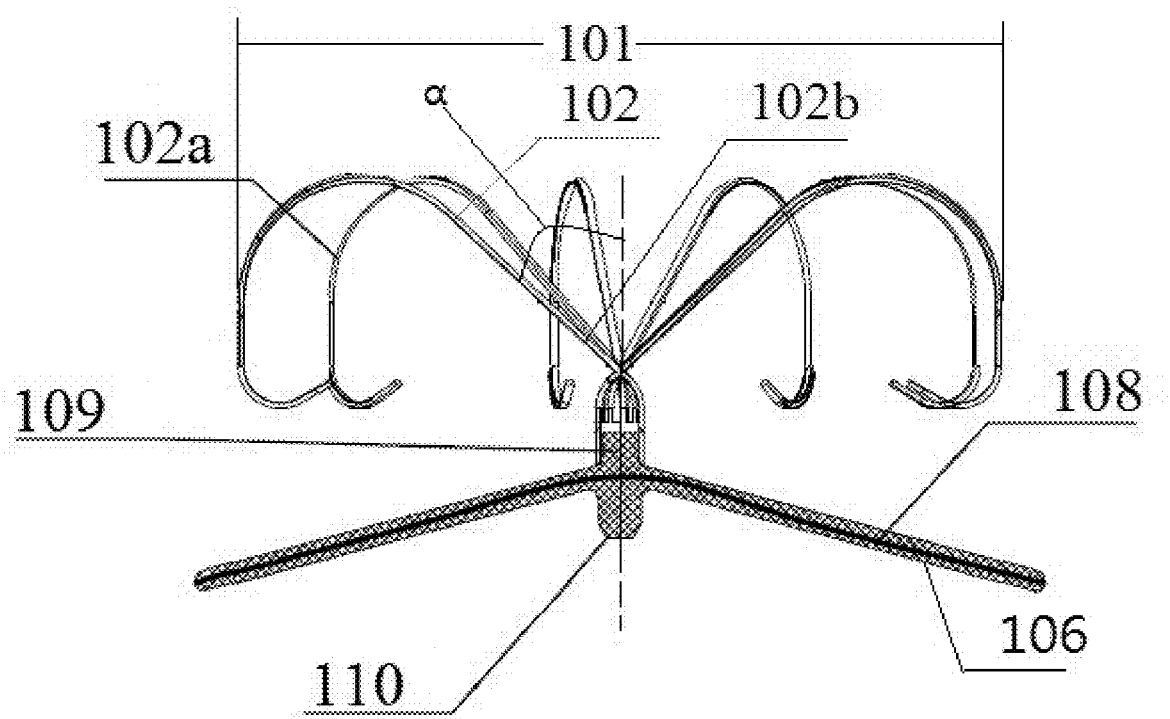
FIG. 1 is a diagram of a preferred embodiment of the left atrial appendage closure apparatus according to the invention.

FIG. 1 describes a left atrial appendage closure apparatus, including a sealing plate 106 and an anchor plate 101 connected to the sealing plate.

The sealing plate is a mesh structure and arranged with a choke membrane 108 inside. The sealing plate's distal end is connected to a tubular member 109 and is connected with the anchor plate by the other end of the tubular member which is opposite the end connected to the sealing plate. The proximal end of the sealing plate is fixed with a fastener 110 and has a structure that can be connected to a convey device.

The end of the tubular member at the other side away from the end connected to the sealing plate is arranged with a plurality of supporting rods 102, the supporting rods originate from the direction away from the sealing plate and the proximal ends 102b of the supporting rods cross the tubular member center to the opposite side, the supporting rods intersect radially to form the anchor plate 101. The angle α between the center axis of the tubular member and the proximal ends 102b of the supporting rods is 40-55° and the distal ends 102a of the supporting rods are in an inwardly curved shape.

Embodiment 2

A left atrial appendage closure apparatus described in FIG. 1 includes a sealing plate 106 and an anchor plate 101 connected to the sealing plate.

The sealing plate is a mesh structure and arranged with a choke membrane 108 inside. The sealing plate's distal end is connected to a tubular member 109 and is connected with the anchor plate by the other end of the tubular member which is opposite the end connected to the sealing plate. The proximal end of the sealing plate is fixed with a fastener 110 and has a structure which can be connected to a convey device.

The end of the tubular member at the other side away from the end connected to the sealing plate is arranged with a plurality of supporting rods 102. The supporting rods originate from the direction away from the sealing plate and the proximal ends 102b of the supporting rods cross the tubular member center to the opposite side. The supporting rods intersect radially to form the anchor plate 101. The angle α between the center axis of the tubular member and the proximal ends 102b of the supporting rods is 40-55° and the distal ends 102a of the supporting rods are in an inwardly curved shape.

When the sealing plate and the anchor plate are expanded, the height of the whole closure apparatus is 12-20 millimeters, the height of the anchor plate is 9-15 millimeters, and the height of the sealing plate is 3-5 millimeters.

Embodiment 3

Figure 2:
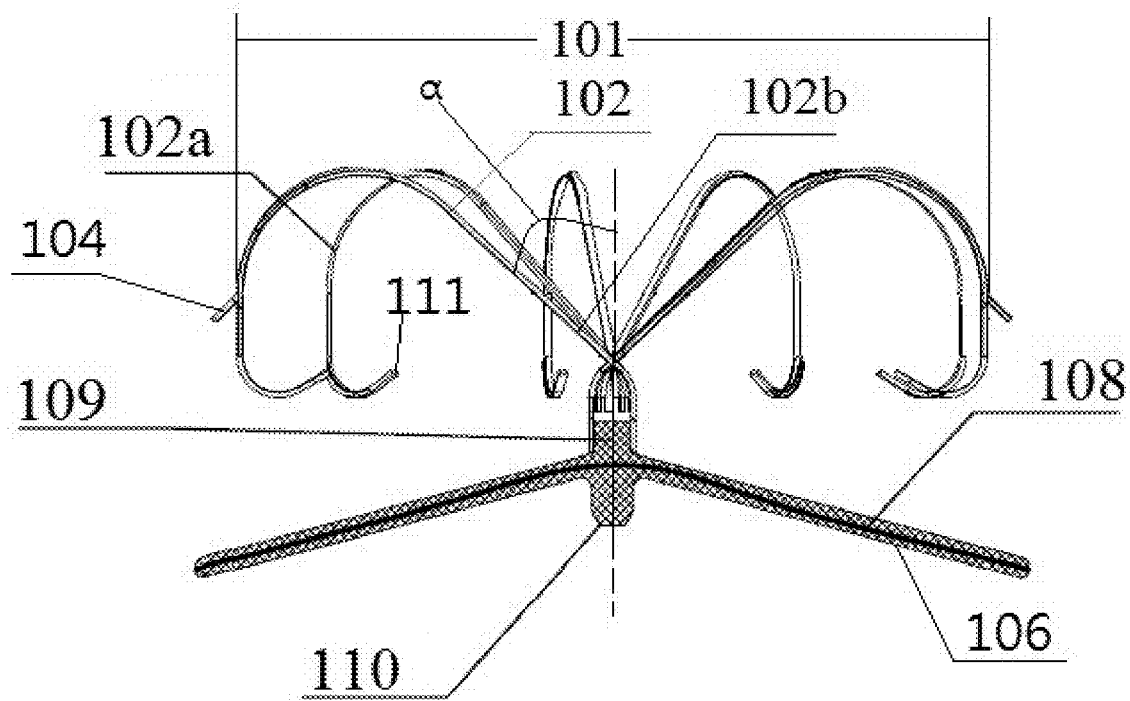
FIG. 2 is a diagram of the third embodiment of the left atrial appendage closure apparatus according to the invention.

A left atrial appendage closure apparatus described in FIG. 2 includes a sealing plate 106 and an anchor plate 101 connected to the sealing plate.

The sealing plate is a mesh structure and arranged with a choke membrane 108 inside. The sealing plate's distal end is connected to a tubular member 109 and is connected with the anchor plate by the other end of the tubular member which is opposite the end connected to the sealing plate, the proximal end of the sealing plate is connected to a fastener 110 and has a structure which can be connected to a convey device.

The end of the tubular member at the other side away from the end connected to the sealing plate is arranged with a plurality of supporting rods 102. The supporting rods originate from the direction away from the sealing plate and the proximal ends 102b of the supporting rods cross the tubular member center to the opposite side. The supporting rods intersect radially to form the anchor plate 101. The angle α between the center axis of the tubular member and the proximal ends 102b of the supporting rods is 40-55° and the distal ends 102a of the supporting rods are in an inwardly curved shape.

The length of the inward bending part of the distal ends 102a of the supporting rods is 1-5 millimeters. The number of the supporting rods is 6. The inward bending part of the distal end of at least one supporting rod has more than one anchor pin 104 on the side near the auricle. The extendable angle between the anchor pin and the supporting rod can be 20-45 degrees. When the anchor plate is expanded, the anchor plate is against the inner wall of the left atrial appendage, and the anchor pin penetrated into the inner wall of the left atrial appendage to stabilize the anchor plate in the left atrial appendage.

The distal ends of the supporting rods are provided with round ball heads 111, and the proximal end of the sealing plate is connected to the fastener, and the structure of the fastener for connecting with the convey device is a screw thread structure.

Embodiment 4

A left atrial appendage closure apparatus described in FIG. 2 includes a sealing plate 106 and an anchor plate 101 connected to the sealing plate.

The sealing plate is a mesh structure and arranged with a choke membrane 108 inside The sealing plate's distal end is connected to a tubular member 109 and is connected with the anchor plate by the other end of the tubular member which is opposite the end connected to the sealing plate. The proximal end of the sealing plate is connected to a fastener 110 and has a structure which can be connected to a convey device.

The end of the tubular member at the other side away from the end connected to the sealing plate is arranged with a plurality of supporting rods 102. The supporting rods originate from the direction away from the sealing plate and the proximal ends 102b of the supporting rods cross the tubular member center to the opposite side. The supporting rods intersect radially to form the anchor plate 101. The angle α between the center axis of the tubular member and the proximal ends 102b of the supporting rods is 40-55° and the distal ends 102a of the supporting rods are in an inwardly curved shape.

The length of the inward bending part of the distal ends 102a of the supporting rods is 1-5 millimeters. The number of the supporting rods is 6. The inward bending part of the distal end of at least one supporting rod has more than one anchor pin 104 on the side near the auricle. The extendable angle between the anchor pin and the supporting rod can be 20-45 degrees. When the anchor plate is expanded, the anchor plate is against the inner wall of the left atrial appendage, and the anchor pin penetrated into the inner wall of the left atrial appendage to stabilize the anchor plate in the left atrial appendage.

The distal ends of the supporting rods are provided with round ball heads 111, and the proximal end of the sealing plate is connected to the fastener, and the structure of the fastener for connecting with the convey device is a screw thread structure.

Figure 3:
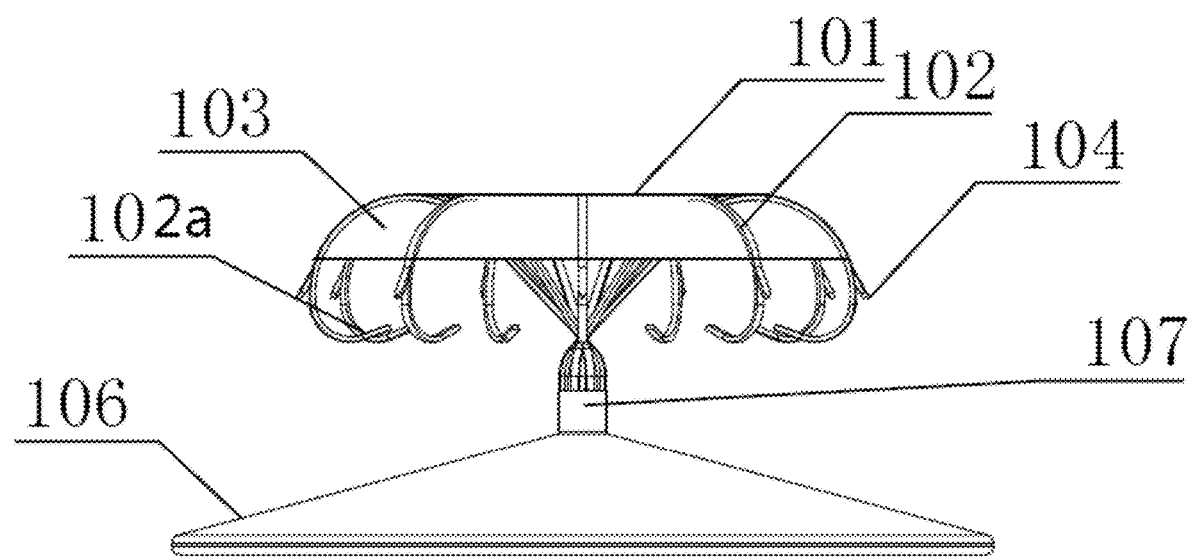
FIG. 3 is a diagram of the fourth embodiment of the left atrial appendage closure apparatus according to the invention.

As shown in FIG. 3, the supporting rods can also be provided with holes to be used to suture the PET (polyethylene terephthalate) choke membrane onto the anchor plate to prevent the outflow of thrombus in the left atrial appendage.

Embodiment 5

A left atrial appendage closure apparatus described in FIG. 2 includes a sealing plate 106 and an anchor plate 101 connected to the sealing plate.

The sealing plate is a mesh structure and arranged with a choke membrane 108 inside. The sealing plate's distal end is connected to a tubular member 109 and is connected with the anchor plate by the other end of the tubular member which is opposite the end connected to the sealing plate. The proximal end of the sealing plate is connected to a fastener 110 and has a structure which can be connected to a convey device.

The end of the tubular member at the other side away from the end connected to the sealing plate is arranged with a plurality of supporting rods 102. The supporting rods originate from the direction away the sealing plate and the proximal ends 102b of the supporting rods cross the tubular member center to the opposite side. The supporting rods intersect radially to form the anchor plate 101. The angle α between the center axis of the tubular member and the proximal ends 102b of the supporting rods is 40-55° and the distal ends 102a of the supporting rods are in an inwardly curved shape.

The length of the inward bending part of the distal ends 102a of the supporting rods is 1-5 millimeters. The number of the supporting rods is 6. The inward bending part of the distal end of at least one supporting rod has more than one anchor pin 104 on the side near the auricle. The extendable angle between the anchor pin and the supporting rod can be 20-45 degrees. When the anchor plate is expanded, the anchor plate is against the inner wall of the left atrial appendage, and the anchor pin penetrated into the inner wall of the left atrial appendage to stabilize the anchor plate in the left atrial appendage.

The distal ends of the supporting rods are provided with round ball heads 111. The proximal end of the sealing plate is fixed with a bolt head. The structure of the fastener for connecting with the convey device is a screw thread structure.

Figure 4A:
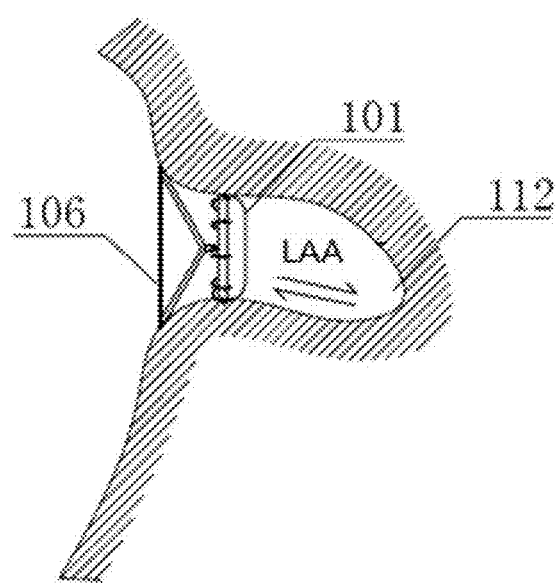
FIG. 4a is a diagram of the fifth embodiment of the left atrial appendage closure apparatus of FIG. 1 positioned in the anatomical structure of the single lobe left atrial appendage.

As shown in FIG. 4a, the sealing plate is slightly larger than the anchor plate in diameter. When the sealing plate is 2-6 mm larger than the anchor plate in diameter, the closure apparatus is suitable for single lobe left atrial appendage.

Figure 4B:
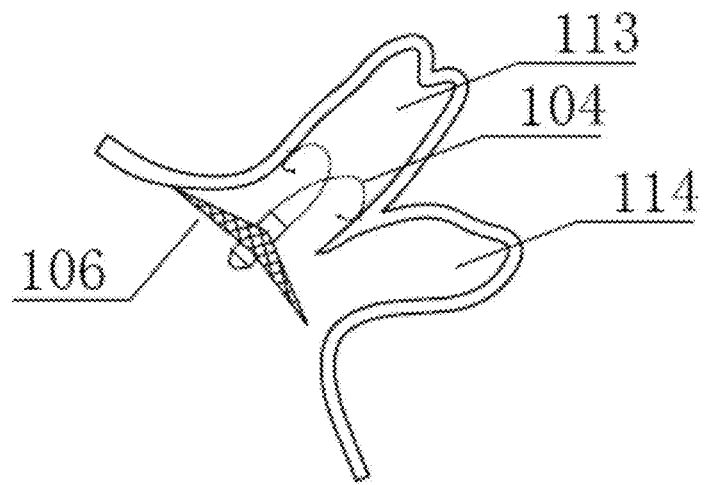
FIG. 4b is a diagram of the fifth embodiment of the left atrial appendage closure apparatus of FIG.
Figure 4C:
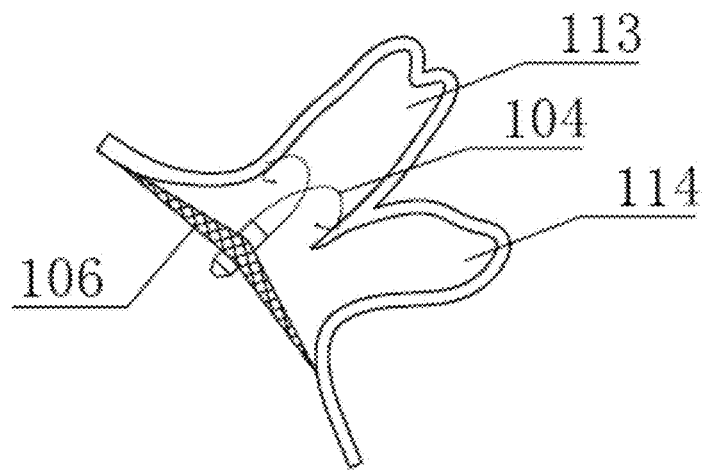
FIG. 4c is a diagram of the fifth embodiment of the left atrial appendage closure apparatus of FIG. 3 positioned in the anatomical structure of the dual-lobe left atrial appendage.

But the dimension above may be difficult to completely seal the dual-lobe left atrial appendage as displayed in FIG. 4b. Therefore, another preferred scheme is shown in FIG. 4c. The sealing plate is slightly larger than the anchor plate in diameter. When the sealing plate is 6-12 mm larger than the anchor plate in diameter, the closure apparatus is more suitable for the dual-lobe left atrial appendage.

Embodiment 6

Figure 5A:
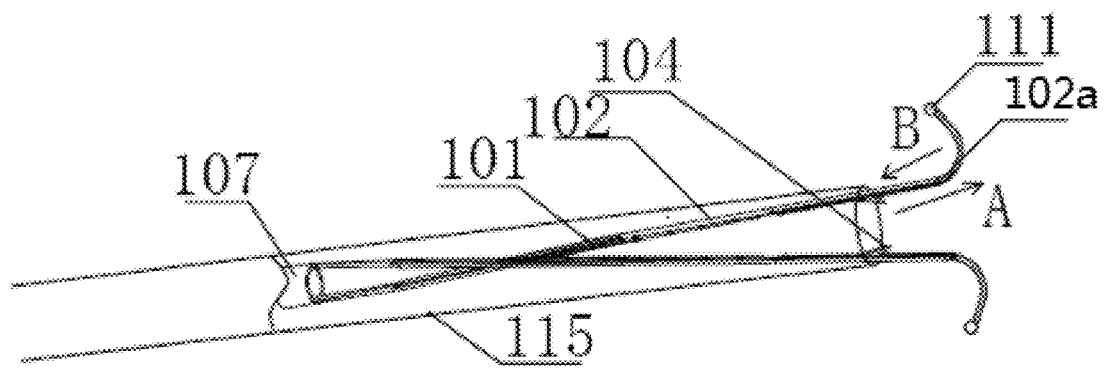
FIG. 5a is a schematic diagram of the anchor plate of the left atrial appendage closure apparatus of FIG. 1 when it emerges from the sheath tube of the convey device.
Figure 5B:
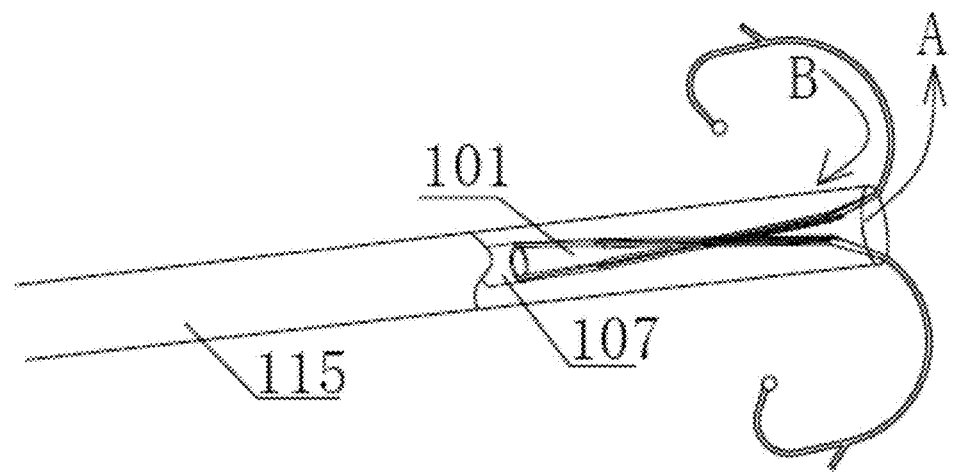
FIG. 5b is a schematic diagram of the anchor plate of the left atrial appendage closure apparatus of FIG. 1 when it is half-way out of the sheath tube of the convey device.
Figure 5C:
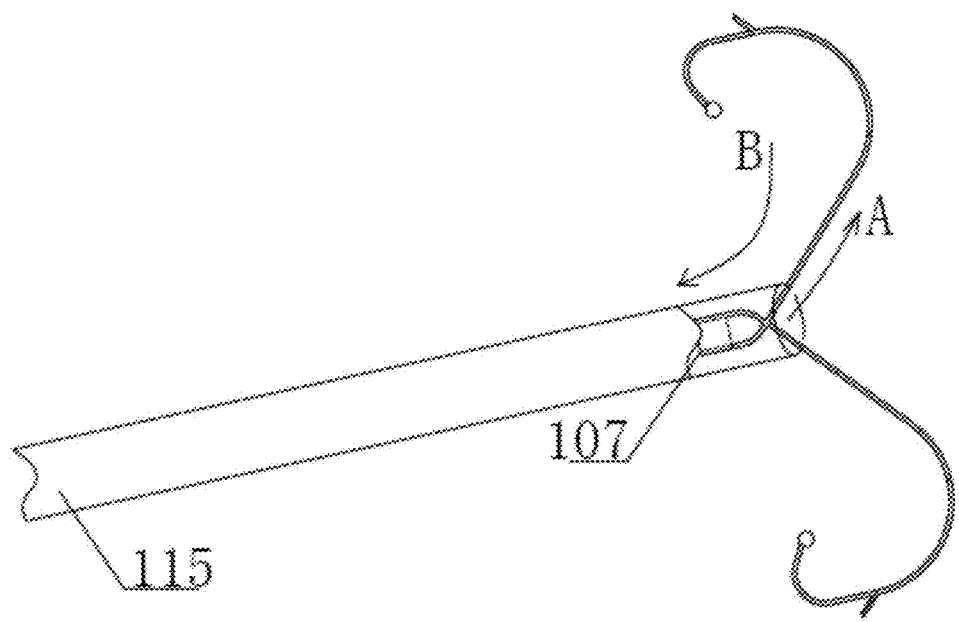
FIG. 5c is a schematic diagram of the anchor plate of the left atrial appendage closure apparatus of FIG. 1 when it is completely out of the sheath tube of the convey device.

As shown in FIGS. 5a, 5b and 5c, the anchor plate 101 has the following characteristics in the processes of being inserted into the sheath tube 115 of the convey device and pulled from the sheath tube 115. In order to clearly demonstrate the processes for the anchor plate 101 to enter and exit the sheath tube, the number of the supporting rods 102 of the anchor plate 101 has been simplified to 2 in FIGS. 5a, 5b and 5c. The supporting rods 102 are straightened in the sheath tube and are in a cross shape. The anchor pins 104 are towards to oblique medial direction opposite the central end 107 of the tubular member. The inner wall of the sheath tube would not be scratched during the pushing process in the sheath tube 115. Under the thrust of the pushing rod, the elbows of the distal ends 102a of the supporting rods are slowly pushed out of the sheath 115 (FIG. 5a) and expand along the direction A. With the continuous pushing of the pushing rod, the supporting rods 102 continue to expand along the direction A as shown in FIG. 5b. At this point, the anchor pins 104 turn about 90 degrees to nearly perpendicular to the pushing rod. The pushing rod continue to exert the impetus and push the anchor plate 101 completely out of the sheath 115, and the supporting rods 102 continue to expand along the direction A as shown in FIG. 5c. At this time, the anchor plate 101 is fully expanded, the anchor pins 104 are turned over about 90 degrees again to position outside the anchor plate 101 and face towards the oblique lateral direction of the central end 107, to penetrate into the inner wall of the left atrial appendage. The closure apparatus is secured in the left atrial appendage cavity.

The process of retrieving the anchor plate 101 is the opposite of each phase of the process of pushing the anchor plate 101 outside the sheath tube 115. The anchor plate 101 is pulled into the sheath tube 115 along the direction B by the pushing rod, wherein the remarkable characteristic is that the anchor pins 104 turn towards the oblique medial direction opposite the central end 107 from the oblique lateral direction of the central end 107 in the expansion process. This process ensures that the anchorage pins 104 does not scrape the wall of the left atrial appendage and enters the sheath tube 115 smoothly. The left atrial appendage closure apparatus in this embodiment is not only able to ensure the repositioning function of the anchor plate 101 in the left atrial appendage, but also greatly reduces the damage to the left atrial appendage wall and reduces the risk and complications of surgery.

Embodiment 7 A Processing Scheme

As shown in FIGS. 1, 2 and 3, the left atrial appendage closure apparatus related to the invention includes the sealing plate 106 and the anchor plate 101 connected with the sealing plate 106, wherein the sealing plate 106 is woven into a mesh structure with nitinol wires and form a plate shape by thermal treatment. Both ends of the sealing plate are fixed with the steel sleeve 109 and the fastener 110 respectively. One end of the sealing plate 106 is linked to the anchor plate 101 with the steel sleeve and the other end is connected with the pushing rod of the convey device by a screw thread structure. The diameter of the sealing plate 106 is about 2-6 mm larger than that of the anchor plate 101, and the inside of the sealing plate 106 is sutured with the chemically modified PET choke membrane 108. The anchor plate 101 is made up of a plurality of supporting rods 102 cut from a nitinol tube, and is treated by thermal treatment with the mould to form the shape shown in the figures. The central end 107 of the anchor plate 101 is welded with the sealing plate 106. According to the requirements of the actual mechanical performance and specifications, the number of supporting rods can be changed. The supporting rods emanated from one inner side of the circle central end 107, cross the center of the central end 107 to the opposite side, and are bent. The supporting rods are arranged in a cross radial way. Holes can also be arranged on the supporting rods 102 to suture the PET choke membrane onto the anchor plate 101 to prevent the outflow of the thrombus in the left atrial appendage. On the supporting rods 102, the shape of the anchor pins 104 is cut out by laser and the angle of the anchor pins 104 is formed by thermal treatment of the mould. The anchor pins 104 oblique laterally and face towards the sealing plate 106. The root of the anchor pins 104 is on the supporting rods 102, the anchor pins 104 open outward automatically in the absence of pressure and are recovered to the supporting rods 102 when under pressure. The distal ends 102a of the supporting rods are curved inward. A spherical head 111 can be arranged at the distal end of the supporting rod 102 to prevent from scratching the inner auricle when the anchor plate 101 is pushed out of the sheath.

Embodiment 8

Figure 6:
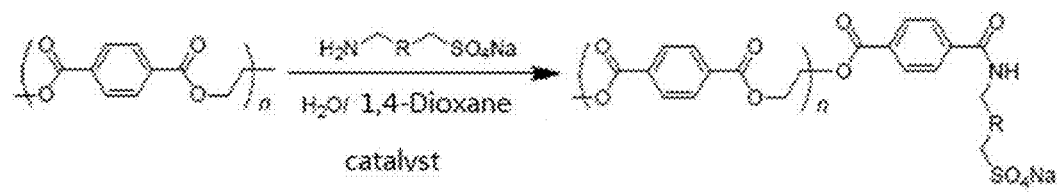
FIG. 6 is a schematic diagram of the chemical reactions for the chemical modification of the choke membrane of the left atrial appendage closure apparatus according to the embodiments of the present invention, in which n=500-5000, R: $CH_2$, $C_2H_4$, $C_3H_6$ or $C_4H_8$.

The PET choke membrane sutured in the sealing plate of the left atrial appendage closure apparatus according to the embodiment is a chemically modified choke membrane. As shown in FIG. 6, the PET choke membrane takes advantage of the reaction to exchange the ester group for an amide group to graft the molecule with sodium sulfonate group on one side onto the surface of the choke membrane. The specific operation is as follows:

50 pieces (50×50 $mm^2$) of PET choke membrane were placed in a 250 mL of round bottom flask., 200 mL of a mixed solvent of water and 1, 4-dioxane with the volume ratio of 5:1 were added., 0.5 g of an alkane with both a terminal amino group and terminal sulfonic group, such as 3-aminopropanesulfonic acid, 4-aminobutanesulfonic acid, 5-aminopentanesulfonic acid or 6-aminohexane sulfonic acid was added, then 1 g of a catalyst, such as sodium hydroxide, potassium hydroxide or ammonia water, was added. The mixture was stirred for 2-24 hours at 50-100° C., The choke membrane was removed after the reaction, and the resulting solution was washed 5 times repeatedly by deionized water and anhydrous alcohol.

Figure 7:
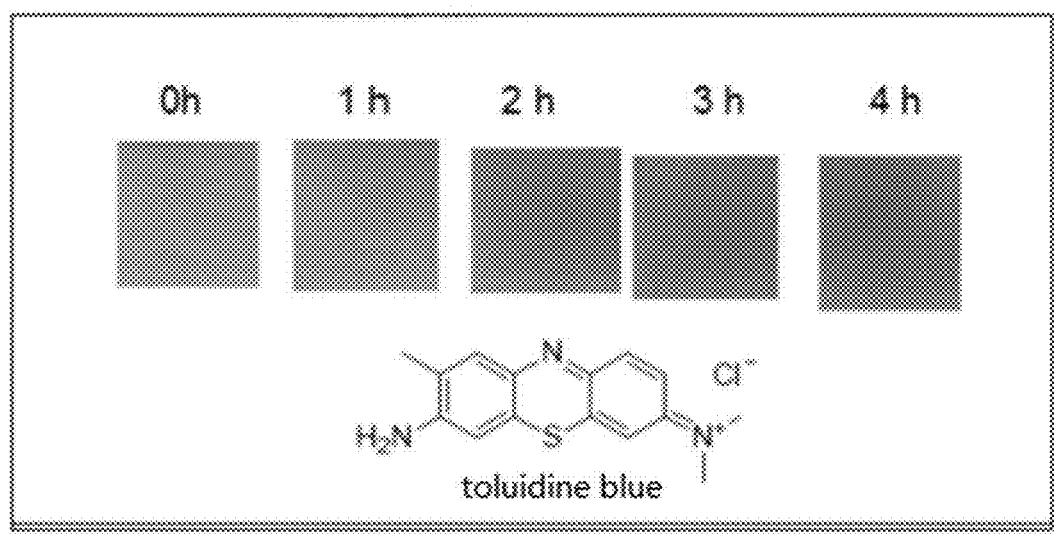
FIG. 7 is a diagram showing the dyeing experiment of the chemical modification of the choke membrane in the left atrial appendage closure apparatus according to the embodiments of the present invention.

As shown in FIG. 7, the PET choke membrane after the chemical reaction was immersed in the toluidine blue dye with positive electrical charge and removed immediately. After many experiments, it was found that the PET choke membrane without chemical modification did not adsorb the toluidine blue dye with positive electrical charge and the adsorbed quantity of the toluidine blue dye also gradually increased with the gradual increasing of the chemical modification time of the PET choke membrane.

Figure 8:
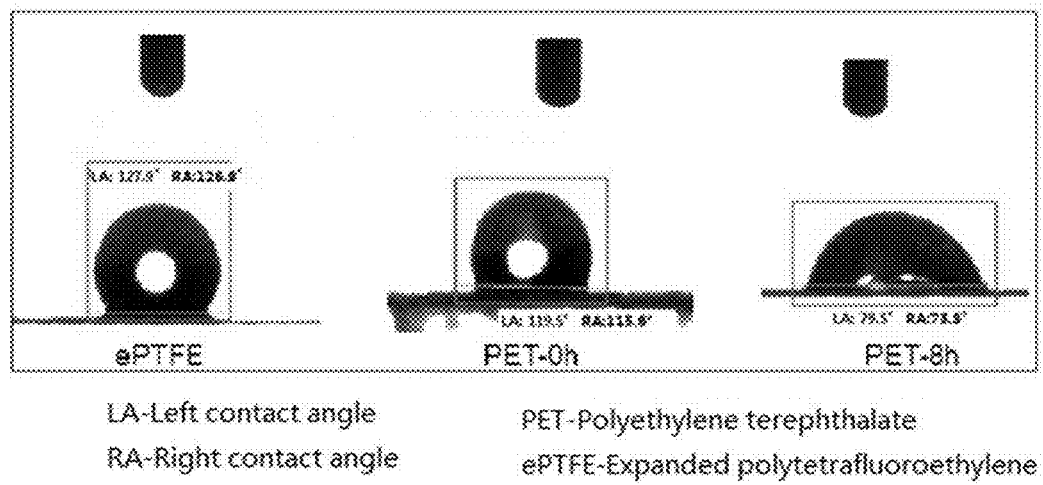
FIG. 8 is a schematic diagram of the contact angle test after chemical modification of the choke membrane of the left atrial appendage closure apparatus according to the embodiments of the present invention. LA is the left contact angle and RA is the right contact angle.
Figure 9:
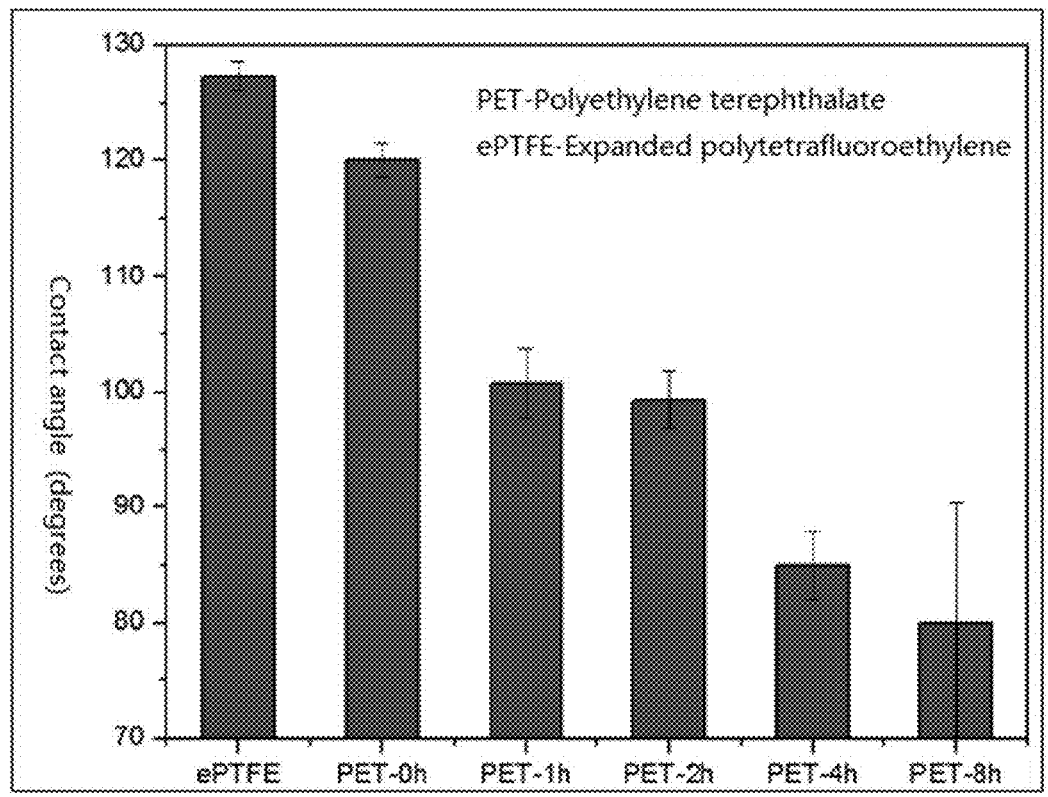
FIG. 9 is a histogram showing the contact angle test results with ePTFE (expanded polytetrafluoroethylene) as the reference, the choke membrane before chemical modification, and choke membrane of the left atrial appendage closure apparatus modified with different chemical modification time according to the embodiments of the invention.

According to the contact angle test results shown in FIGS. 8 and 9, the contact angle between the chemically modified PET choke membrane and the water droplet was 76.5±3 degrees (as displayed in PET-8 h histogram), which was 41 degrees smaller than that of the unmodified PET choke membrane, and 51 smaller than that of the super hydrophobic ePTFE film. According to the test results, the hydrophilicity of the modified PET film was greatly enhanced, which was beneficial to improve the hydrophilicity and biocompatibility of the choke membrane, to achieve rapid endothelialization and to reduce the risk of thrombosis associated with the closure apparatus.

Embodiment 9. Animal Experiment

Figures 10A, 10B:
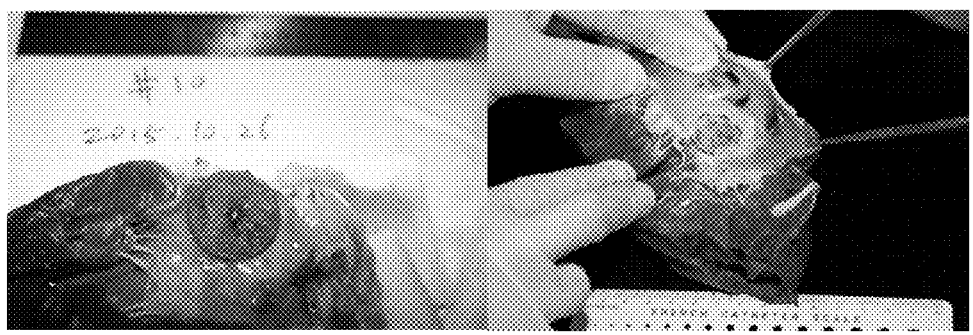
FIG. 10a and FIG. 10b are respectively the anatomic image 1 day and 1 month after the surgery.
Figure 11:
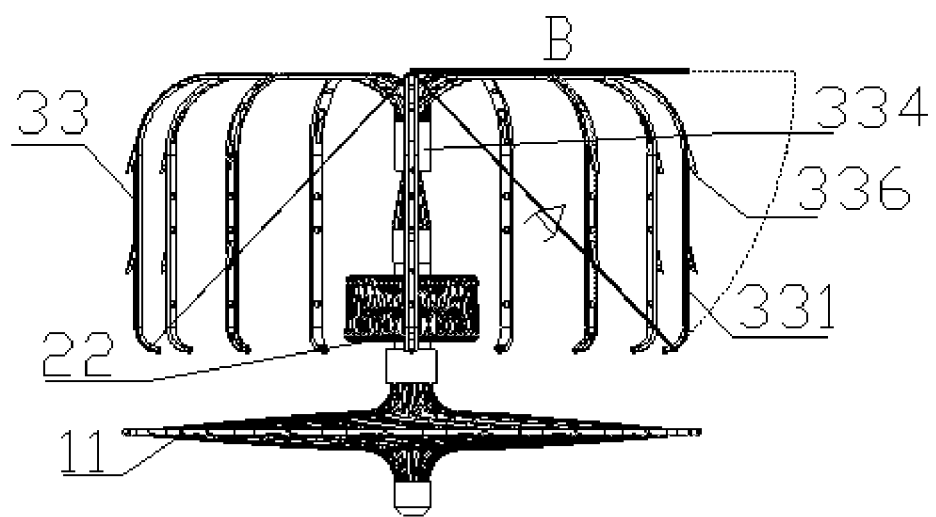
FIG. 11 is a schematic diagram of the closure apparatus according to CN104352261A when the apparatus is expanded or unexpanded.

The closure apparatus with the chemical modified PET choke membrane in the embodiment according to the invention was adopted and the experimental method was as follows:

All the experimental dogs received percutaneous left atrial appendage occlusion under general anesthesia. They started fasting 12 h before the surgery and were placed on the operating table under restraint after anesthesia. The tracheal intubation was conducted to connect the respirator for mechanical ventilation with indwelling transesophageal ultrasound probe. The electrocardiogram monitoring was connected and venous access in the left lower extremities was established. If the anatomic abnormalities of the heart were observed in the transesophageal echocardiogram, the surgery would be stopped and the other experimental dog was replaced. For dogs with normal heart anatomy, the shape of their left atrial appendage was observed by transesophageal echocardiography and the diameter of left atrial appendage was measured to select the closure apparatus with a diameter about 15-35% larger than the measured diameter. Routine disinfection was performed and the sterile towels were spread. The right femoral artery and vein were punctured with the Telma puncture suit, and the 6F femoral sheath was retained. Through the femoral artery sheath, the 5F pigtail catheter was delivered to the aortic sinus to mark the position of the aortic sinus to avoid atrial septal puncture into the aortic sinus. Through the femoral vein sheath, the atrial septal puncture needle (SL1, St Jude Medical, US) and the matched atrial septal puncture sheath were delivered to complete the transseptal puncture under the guidance of the transesophageal echocardiography. After successful puncture, 80-100 U/kg of heparin was given, and the atrial septal puncture needle was withdrawn. The long exchange steel wire was delivered to the left pulmonary vein to exchange 8-10F closure apparatus delivery sheath to the opening part of the left atrial appendage, and the pigtail catheter was delivered to the left atrial appendage for conducting the left atrial appendage angiography and measuring the opening diameter of the left atrial. the sealing plate of the closure apparatus with the diameter about 15-35% larger than the measurement value was selected in combination with the transesophageal echocardiography results, and the closure strategy was determined according to the lobe form of the left atrial appendage. The sealing plate selected was fixed on the head of the pushing rod by a nut, when the air in the closure apparatus and the conveying sheath was exhausted. The pushing rod was slowly forwarded and part of the anchor plate was pushed out of the delivery sheath before entering the opening of the left atrial appendage. The conveying sheath and the pushing rod as whole were pushed to the anchoring area of the left atrial appendage. When their head reached the anchoring area of the opening of the left atrial appendage, the pushing rod was fixed and the conveying sheath withdrawn gradually. The deployed closure apparatus was observed by the transesophageal echocardiography and angiography of the left atrial appendage, while the pushing and pulling tests were performed to check whether the deployed closure apparatus was secure and stable. If the closure apparatus was in the proper position and the fixation was secure, the closure apparatus would be released. If the complete occlusion failed or the extension shape of the closure apparatus was improper, the closure apparatus was completely retrieved into the conveying sheath for another attempt at delivery until the ideal sealing effect was achieved, then the closure apparatus could be released. After the surgery, the experimental dogs routinely took aspirin and were followed up on regularly. The anatomical images (FIGS. 10a and 10b) on the 1st day and 1 month after surgery display that in the 1-2 months, the endothelial cells were uniformly endothelialized on the closure apparatus and there was no obvious thrombosis forming, which was significantly more effective than the existing technology in endothelialization and thrombosis inhibition.

Therefore, the embodiments according to the present invention has the following advantages:

The anchor plate of the left atrial appendage closure apparatus according to the invention is in a depression shape, which helps the sheath tube of the convey device to deliver and retrieve the anchored plate. When the closure apparatus is delivered or retrieved by the sheath tube, the anchor plate in the depression shape has the smaller diameter in the folding process than in the expansion process, which enables the anchor plate to slowly fold into the sheath tube of the convey device so as to avoid the damage of the left atrial appendage and improve the safety efficiency.

The anchor plate of the left atrial appendage closure apparatus according to the invention has little structure deformation, is stable, and has excellent fatigue resistance for permanent implantation and adaptable to the left atrial appendage cavity with various shapes and sizes.

The two-part design of the left atrial appendage closure apparatus according to the present invention enables the closure apparatus to adapt to various forms and dimensions of the left atrial appendage.

The left atrial appendage closure apparatus according to the invention has the advantages of stable anchorage and effective occlusion of the left atrial appendage.

The left atrial appendage closure apparatus according to the invention is applicable to not only occlude the single lobe left atrial appendage, but also occlude the dual-lobe left atrial appendage.

The left atrial appendage closure apparatus according to the invention can be repeatedly positioned. In some cases, if the placement is not good enough and without releasing the convey device, such as the pushing rod, the closure apparatus can be retrieved to the sheath tube and repositioned until the satisfactory anchoring and occlusion effects are achieved, which greatly reduces surgery risks.

The left atrial appendage closure apparatus according to the invention can use a small conveying system to further reduce the damage to the blood vessel by the convey devices in the surgery process.

The left atrial appendage closure apparatus according to the invention is flexibly connected with the pushing rod, which greatly reduces the tension exerted by the pushing rod to the closure apparatus and makes the placement of the closure apparatus more accurate and precise.

The choke membrane of the left atrial appendage closure apparatus according to the invention is chemically treated to generate negative surface ionization, which not only reduces platelet adhesion on the surface of the sealing plate, but also improves hydrophilicity and biological compatibility of the choke membrane, as well as achieves rapid endothelialization, which reduces the closure apparatus associated thrombosis risks.

The above mentioned is only a preferred embodiment of the present invention, and should not be used to restrict the invention. Any modification, substitution and improvement within the spirit and principles of the invention should be included in the protection scope of the invention.

The invention claimed is:

1. A left atrial appendage closure apparatus, comprising:
a sealing plate, an anchor plate and a tubular member,
the tubular member having a first end and a second end, wherein the first end of the tubular member is secured to the anchor plate, wherein the second end of the tubular member is secured to the sealing plate; the tubular member comprising a sleeve;
wherein the anchor plate comprises a plurality of supporting rods, each supporting rod of the plurality of supporting rods having a proximal end and a distal end, the proximal end of each supporting rod being connected to the first end of the tubular member, the distal end of the supporting rod extending away from the tubular member,
wherein when the apparatus is expanded, each supporting rod projects in a direction traversing an axial center opening of the tubular member without extending into a lumen of the tubular member, whereby the supporting rods converge the plurality of supporting rods being positioned radially along a circumference of the tubular member
wherein when the apparatus is expanded, each support rod forms an angle α with the cylindrical axis of the tubular member, and wherein the angle α is 40-55°, and wherein when the apparatus is expanded, the distal end of each support rod is proximal to where the plurality of support rods converge.

2. The left atrial appendage closure apparatus according to claim 1, wherein when the apparatus is expanded, the apparatus has a height of 12-20 millimeters, the anchor plate has a height of 9-15 millimeters, and the sealing plate has a height of 3-5 millimeters.

3. The left atrial appendage closure apparatus according to claim 1, wherein the distal end of at least one of the plurality of supporting rods is bent.

4. The left atrial appendage closure apparatus according to claim 1, wherein the plurality of supporting rods comprises an odd number of supporting rods.

5. The left atrial appendage closure apparatus according to claim 1, wherein at least one of the plurality of supporting rods has one or more anchor pins.

6. The left atrial appendage closure apparatus according to claim 5, wherein when the apparatus is expanded in a left atrial appendage, the anchor plate is configured to contact an inner wall of the left atrial appendage, and the anchor pin is configured to insert into the inner wall of the left atrial appendage to stabilize the apparatus.

7. The left atrial appendage closure apparatus according to claim 1, wherein the sealing plate comprises a choke membrane.

8. The left atrial appendage closure apparatus according to claim 7, further comprising a second choke membrane sutured to the plurality of supporting rods.

9. The left atrial appendage closure apparatus according to claim 7, wherein the choke membrane comprises unmodified or chemically modified PET.

10. The left atrial appendage closure apparatus according to claim 9, wherein the choke membrane comprises chemically modified PET having sodium sulfonate group on a surface of the choke membrane.

11. The left atrial appendage closure apparatus according to claim 1, wherein when the apparatus is expanded, the sealing plate has a diameter that is greater than that of the anchor plate.

12. The left atrial appendage closure apparatus according to claim 1, wherein the sealing plate comprises a mesh structure woven by memory alloy wires.

13. The left atrial appendage closure apparatus according to claim 1, wherein when the apparatus is expanded, each supporting rod first extends away from the tubular member, and then extends toward the tubular member after a bending, such that parts of each supporting rod extending toward the tubular member form a periphery of the anchor plate.

14. The left atrial appendage closure apparatus according to claim 13, wherein the sealing plate and the distal end of each supporting rod are at opposite sides of the tubular member.

15. The left atrial appendage closure apparatus according to claim 1, wherein the plurality of supporting rods and the tubular member are made of a tube.

16. The left atrial appendage closure apparatus according to claim 1, wherein the proximal ends of the plurality of supporting rods are positioned at intervals along a circumference of the tubular member.

17. An implant apparatus, comprising:
an anchor plate and a tubular member, wherein the anchor plate is secured to the tubular C member and for anchoring in a body cavity, the tubular member comprising a sleeve,
wherein the anchor plate comprises a plurality of supporting rods, each supporting rod of the plurality of supporting rods having a proximal end and a distal end, the proximal end of each supporting rod being connected to one end of the tubular member, the distal end of the supporting rod extending away from the tubular member,
wherein when the apparatus is expanded, each supporting rod projects in a direction traversing an axial center opening of the tubular member without extending into a lumen of the tubular member,
whereby the supporting rods converge, the plurality of supporting rods being positioned radially along a circumference of the tubular member wherein when the apparatus is expanded, each support rod forms an angle α with the cylindrical axis of the tubular member, and wherein the angle α is 40-55°, and
wherein when the apparatus is expanded, the distal end of each support rod is proximal to where the plurality of support rods converge.

18. The implant apparatus according to claim 17, wherein the plurality of supporting rods comprises an odd number of supporting rods.

19. The implant apparatus according to claim 17, wherein when the apparatus is expanded, each supporting rod first extends away from the tubular member, and then extends toward the tubular member after a bending, such that parts of each supporting rod extending toward the tubular member form a periphery of the anchor plate.

20. A left atrial appendage closure apparatus, comprising:
a sealing plate, an anchor plate and a tubular member,
the tubular member comprising a sleeve, the tubular member having a first end and a second end, wherein the first end of the tubular member is secured to the anchor plate, wherein the second end of the tubular member is secured to the sealing plate;
wherein the anchor plate comprises a plurality of supporting rods, each supporting rod of the plurality of supporting rods having a proximal end and a distal end, the proximal end of each supporting rod being connected to the first end of the tubular member, the distal end of the supporting rod extending away from the tubular member,
wherein when the apparatus is expanded, the plurality of supporting rods converge towards a cylindrical axis of the tubular member and intersect to form the anchor plate with a center depression, the plurality of supporting rods being positioned radially along a circumference of the tubular member
wherein when the apparatus is expanded, each support rod forms an angle α with the cylindrical axis of the tubular member, and wherein the angle α is 40-55°, and
wherein when the apparatus is expanded, the distal end of each support rod is proximal to where the plurality of support rods converge.

\* \* \* \* \*